United States Patent [19]
Tachon et al.

[11] Patent Number: 5,985,293
[45] Date of Patent: *Nov. 16, 1999

[54] ANTIOXIDATIVE DERMOCOSMETIC COMPOSITIONS COMPRISING VERY LOW DOSAGES OF MELATONIN/ANALOGS

[75] Inventors: Pierre Tachon, Antony; Francis Pruche, Paris; Catherine Gerst, Asnieres/Seine; Jean-François Nadaud, Clamart; Lionel Breton, Versailles, all of France

[73] Assignee: Societe L'oreal S.A., Paris, France

[ * ] Notice: This patent is subject to a terminal disclaimer.

[21] Appl. No.: 08/900,109

[22] Filed: Jul. 25, 1997

[30] Foreign Application Priority Data

Jul. 25, 1996 [FR] France .................................. 96 09387

[51] Int. Cl.$^6$ ................. A61K 7/00; A61K 7/40
[52] U.S. Cl. ................ 424/401; 424/70.1; 424/70.5; 514/415
[58] Field of Search ............. 514/415; 548/504; 424/59, 70.1, 70.5, 401

[56] References Cited

U.S. PATENT DOCUMENTS 4,746,674  5/1988  Pierpaoli et al. .................... 514/415
5,560,917  10/1996 Cohen et al. ....................... 424/401

FOREIGN PATENT DOCUMENTS

86/05093  9/1986  WIPO .
87/00432  1/1987  WIPO .
93/07870  4/1993  WIPO .

OTHER PUBLICATIONS

Reiter, R. J. Interactions of pieal hormone melatonin with oxygen–centered free radicals: a brief review, Brazilian J. Med. Res. 26:1141–1155, 1993.

*Primary Examiner*—Thurman K. Page
*Assistant Examiner*—Lakshmi Channavajjala
*Attorney, Agent, or Firm*—Burns, Doane, Swecker & Mathis, L.L.P.

[57] ABSTRACT

Topically applicable dermocosmetic compositions for improving or maintaining the appearance of human skin or the scalp, comprise a minor antioxidant effective amount of melatonin or analog thereof, formulated into a topically applicable, cosmetically/dermatologically acceptable vehicle, diluent or carrier therefor, such minor antioxidant effective amount being less than $10^{-4}\%$ by weight relative to the total weight thereof, e.g., no greater than $0.5 \times 10^{-4}\%$ or ranging from $10^{-12}\%$ to $10^{-15}\%$ by weight thereof.

13 Claims, No Drawings

ANTIOXIDATIVE DERMOCOSMETIC COMPOSITIONS COMPRISING VERY LOW DOSAGES OF MELATONIN/ANALOGS

CROSS-REFERENCE TO COMPANION APPLICATIONS

Copending applications Ser. No. 08/900,828 [Attorney Docket No. 016800-156] and Ser. No. 08/900,832 [Attorney Docket No. 016800-159], each filed concurrently herewith and each assigned to the assignee hereof.

BACKGROUND OF THE INVENTION

1. Technical Field of the Invention

The present invention relates to novel dermocosmetic compositions comprising judiciously selected very low dosages of melatonin or analog thereof, having improved antioxidant activity, and which are particularly well-suited for improving or maintaining the appearance of human skin or the scalp.

2. Description of the Prior Art

The role of cellular oxidation in aging of the skin, both intrinsic and extrinsic aging, in particular photoinduced aging, is known to this art. Such aging of the skin is reflected in various clinical signs and conditions, in particular the appearance of fine lines and deep wrinkles which increase or are accentuated with age. Moreover, the appearance of the skin or the scalp deteriorates. The skin complexion is generally modified and diffuse irritations and occasionally telangiectasia may exist on certain areas of the skin. Another clinical sign of aging is the dry and coarse appearance of the skin, which is due essentially to more pronounced desquamation. Lastly, a loss of firmness and tonicity of the skin are observed, which, as for the wrinkles and fine lines, is at least partly explained by dermal and epidermal atrophy, as well as by a flattening out of the formation. It is thus observed that the clinical signs of aging of the skin result essentially from dysfunction of the principal biological mechanisms involved in the skin.

Preventing or treating aging of the skin, both intrinsic and extrinsic aging, and the clinical signs described above is essentially a matter of maintaining or improving the appearance of the skin or the scalp.

Various antioxidants capable of preventing or treating aging of the skin are described in the prior art, for example melatonin (EP-214,254).

Melatonin, or N-acetyl-5-methoxytryptamine, known especially for its activity on the circadian rhythm which regulates the production of hormones, is also described for its antioxidant activity (Reiter R. J., *Verhandlung der Deutschen Zoologischen Gesellschaft*, 87 (2), 195–204 (1994); Reiter R. J. et al., *Neuroendocrinoll Letter*, 15 (1–3), 103–113 (1993); Reiter R. J. et al., *J. Pineal Res.*, 18 (1), 1–11 (1995)), in particular its anti-free-radical activity (Reiter R. J. et al., *Brazilian Journal of Medical and Biological Research*, 26 (22), 1141–1155 (1993)). Most of the studies of the antioxidant properties of melatonin relate to the oxidation phenomena associated with aging of the brain (Poeggeler B. et al., *J. Pineal Res.*, 14 (4), 151–168 (1993); Cagnoli C. M. et al., *J. Pineal Res.*, 18 (4), 222–226 (1995); Melchiorri D. et al., *FASEB J.*, 9 (12), 1205–1210 (1995); Sewerynek E. et al., *Neuroscience Letters*, 195, (3), 203–205 (1995)).

Melatonin has also been described for dermocosmetic applications in order to improve the appearance of the skin (JP-61/221,104; WO 86/05093), or to protect the skin against the deleterious effects of irradiation with UV rays (EP-0,438,856; E. Bangha et al., *Dermatology*, 191, [2], 176 (1995)). It is recommended to use melatonin at concentrations of between $10^{-4}$ and 10% by weight relative to the total weight of the composition.

Thus, WO-86/05093 describes a cosmetic composition comprising melatonin to increase the skin sensitivity towards estrogens, in particular for the treatment of acne or the prevention of hair loss. The amounts of melatonin recommended in that application are generally between $10^{-4}$% and more than 1% by weight relative to the total weight of the composition. The only two specific examples of compositions, a lotion for the treatment of acne and a solution for preventing hair loss, comprise 10% and 0.1% by weight of melatonin, respectively.

Similarly, EP-438,856, relating to compositions for protection of the skin against the deleterious effects of irradiation with UV rays, recommends amounts of melatonin of between 1% and 10% by weight for topical compositions, the only example of this type of composition comprising 10% melatonin.

JP-61/221,104 describes a cleansing milk comprising 10% melatonin in order to attenuate skin roughness. As regards the above two publications, the antioxidant action of melatonin is not mentioned for the effects studied.

The article by Bangha et al. (*Dermatology*, 191, [2], 176 (1995)) describes a gel containing melatonin which is capable of reducing the erythema induced by UV, probably on account of its anti-free-radical activity. The concentrations tested are 0.05, 0.1 and 0.5%, the authors recommending a concentration of 0.5%.

SUMMARY OF THE INVENTION

It has now unexpectedly been determined that melatonin is antioxidatively ineffective at doses corresponding to the concentrations described in the literature, but is indeed effective as an antioxidant at lower doses, approximating physiological doses.

Briefly, the present invention features topically applicable dermocosmetic compositions comprising melatonin or analog thereof, at concentrations less than those recommended in the prior art, in order to attain an identical, or even enhanced, antioxidant activity.

DETAILED DESCRIPTION OF BEST MODE AND SPECIFIC/PREFERRED EMBODIMENTS OF THE INVENTION

More particularly according to the present invention, it has now been demonstrated on normal human keratinocytes in culture that melatonin exhibits no antioxidant activity at a concentration of $10^{-5}$ M, but is active at concentrations less than or equal to $10^{-7}$ M.

Similarly, antioxidant activity of hormonal type at the cellular level has also been demonstrated, in particular an activity of inducing the expression of the mRNAs of glutathione peroxidase (GSH), the principal enzyme in the antioxidant defense of the skin, at physiological doses ranging from $10^{-9}$ to $10^{-15}$ M.

The present invention thus features a topical composition comprising melatonin or analog thereof and a cosmetically or pharmaceutically acceptable support (vehicle, diluent or carrier therefor), in which the amount of melatonin or analog thereof is an amount which is suitable to permit, after topical application and via dermal delivery, the passage of physiological doses of melatonin or analog thereof, of between $10^{-15}$ and $10^{-7}$ M, into the skin.

Too, the present invention features dermocosmetic compositions comprising melatonin or analog thereof formulated into topically applicable, cosmetically or pharmaceutically acceptable vehicles, diluents or carriers therefor, in which the amount of melatonin or of an analog thereof is strictly less than $10^{-4}\%$ by weight relative to the total weight of the composition.

The amount of melatonin or analog thereof in the compositions according to the invention is preferably less than or equal to $0.5 \times 10^{-4}\%$ by weight, more preferably less than or equal to $10^{-10}\%$ by weight, advantageously between $10^{-12}\%$ and $10^{-5}\%$ by weight relative to the total weight of the composition.

Exemplary melatonin "analogs" include, in particular, its derivatives such as 5-methoxytryptamine, 5-methoxytryptophan, 5-methoxytryptophol, 5-methoxyindole-3-acetic acid and 6-hydroxymelatonin. Also representative are melatoninergic agonists such as those described in WO-95/17405, EP-0,447,285, EP-0,527,687, EP-0,530,087 and EP-0,591,057. These compounds are of natural or synthetic origin.

The topically applicable compositions of the invention comprising melatonin or analog thereof comprise a cosmetic or dermatological composition and may exist in any pharmaceutical form for topical application which is normal in this art, and the physiologically acceptable vehicle, diluent or carrier may comprise any common support for a cosmetic or dermatological composition. The subject compositions may be in the form, in particular, of an aqueous solution or oily suspension or dispersion of the lotion or serum type, emulsions of liquid or semi-liquid consistency of the milk type, obtained by dispersion of a fatty phase in an aqueous phase (O/W) or, conversely, (W/O), or suspensions or emulsions of soft consistency of the cream or aqueous or anhydrous gel type, or, alternatively, microcapsules or microparticles, or vesicle dispersions of ionic and/or non-ionic type. These compositions are formulated via the usual techniques.

The amounts of the various constituents of the subject compositions are those conventionally employed in this art.

Such compositions, in particular, constitute cleansing, protective, treatment or care creams for the face, for the hands, for the feet, for the major anatomical folds or for the body (for example day creams, night creams, makeup-removing creams, foundation creams and antisun/sunscreen creams), fluid foundations, makeup-removing milks, protective or body care milks, antisun/sunscreen milks, skincare lotions, ointments, gels or mousses, such as cleansing lotions, antisun/sunscreen lotions, artificial tanning lotions, compositions for the bath, deodorizing compositions comprising a bactericide, aftershave gels or lotions, hair-removing creams, compositions to prevent insect bites, pain-relief compositions, compositions for treating certain skin diseases such as eczema, rosacea, psoriasis, lichens and severe pruritus.

When the composition is an emulsion, the proportion of the fatty phase may range from 5% to 80% by weight, and preferably from 5% to 50% by weight, relative to the total weight of the composition. The oils, the waxes, the emulsifiers and the co-emulsifiers formulated into the compositions in emulsion form are selected from among those conventionally employed in the cosmetics art. The emulsifier and the co-emulsifier are advantageously present in the composition in a proportion ranging from 0.3% to 30% by weight, and preferably from 0.5 to 20% by weight, relative to the total weight of the composition. The emulsifier may, moreover, contain lipid vesicules.

When the composition is a solution or an oily gel, the fatty phase may represent more than 90% of the total weight of the composition.

In known manner, the cosmetic or dermatological composition may also contain additives and adjuvants that are common in the cosmetic or dermatological arts, such as hydrophilic or lipophilic gelling agents, hydrophilic or lipophilic additives, preservatives, antioxidants, solvents, fragrances, fillers, screening agents, odor absorbers and dyestuffs and colorants. The amounts of these various additives and adjuvants are those conventionally used in these fields and, for example, constitute from 0.01% to 10% of the total weight of the composition. Depending on their nature, these additives and adjuvants may be introduced into the fatty phase, into the aqueous phase, and/or into the lipid spherules.

Exemplary oils or waxes include mineral oils (liquid petroleum jelly), plant oils (liquid fraction of karite butter, sunflower oil), animal oils (perhydrosqualene), synthetic oils (Purcellin oil), silicone oils or waxes (cyclomethicone) and fluoro oils (perfluoropolyethers), beeswax, carnauba wax or paraffin wax. Fatty alcohols and fatty acids (stearic acid) may be added to these oils.

Exemplary emulsifiers include, for example, glyceryl stearate, polysorbate 60 and the mixture of PEG-6/PEG-32/glycol stearate marketed, for example, under the trademark Tefose® 63 by Gattefosse.

Exemplary solvents include the lower alcohols, in particular ethanol and isopropanol, and propylene glycol.

And exemplary hydrophilic gelling agents include carboxyvinyl polymers (carbomer), acrylic copolymers such as acrylate/alkyl acrylate copolymers, polyacrylamides, polysaccharides such as hydroxypropylcellulose, natural gums and clays, and representative lipophilic gelling agents include the modified clays such as bentones, metal salts of fatty acids such as aluminum stearates, hydrophobic silica, ethylcellulose and polyethylene.

Insofar as they do not interfere with the activity of melatonin and analogs thereof, the compositions according to the invention may contain other active agents intended, in particular, to prevent and/or treat skin conditions/afflictions.

The compositions according to the invention are particularly well suited for preventing or treating oxidative stress of the skin and/or systems associated therewith, in particular associated with UV irradiation, with aging, with inflammation, with alopecia, etc.

In order to further illustrate the present invention and the advantages thereof, the following specific examples are given, it being understood that same are intended only as illustrative and in nowise limitative.

In the composition examples to follow, all parts and percentages are given by weight.

EXAMPLE 1

Study on normal human keratinocytes in culture

Normal human keratinocytes were incubated for one hour in the presence of melatonin at various concentrations. The cells were subjected to a radical stress initiated by UV-A radiation (10 J/cm$^3$). The hydroperoxides were detected in the cells by a fluorescent probe (CM-H2DCF-DA, marketed by Molecular Probe).

The results are reported in Table I below, compared to controls cultured in the absence of melatonin, with or without irradiation, and to a reference (cells cultured in the presence of a combination of 0.5 mg/ml of vitamin C and 0.5 mg/ml of GSH).

TABLE I

| Melatonin Concentration (M) | Fluorescence units measured | % Protection |
|---|---|---|
| $10^{-5}$ M | 1123 ± 50 | — |
| $10^{-7}$ M | 863 ± 152 | 34.0 |
| $10^{-9}$ M | 802 ± 123 | 42.5 |
| irradiated control | 1135 ± 90 | — |
| non-irradiated control | 350 ± 7 | — |
| reference (Vit C + GSH) | 932 ± 10 | 26.0 |

These results demonstrate a zero antioxidant activity at melatonin doses of $10^{-5}$ M, namely, corresponding to the compositions described in the prior art, and the appearance of considerable antioxidant activity at lower concentrations.

EXAMPLE 2

Study of the stimulation of the production of GSH-Px in interfollicular keratinocytes Stimulation of the activity of GSH-Px Normal human keratinocytes were incubated for increasing periods (1 h,30 min, 3 h and 6 h) in the presence of melatonin at concentrations ranging from $10^{-6}$ to $10^{-17}$ M. The control corresponded to keratinocytes incubated in the absence of melatonin.

After incubation, the keratinocytes were taken up in a homogenization buffer. The keratinocytes were subjected to three cycles of freezing/thawing, the extract was then centrifuged and the GSH-Px in the supernatant was assayed by the TBH technique described by D. E. Paglia and W. N. Valentine (*J. Lab. Clin. Med.*, 70, 158–169 (1967)).

Stimulation of the activity of GSH-Px was observed at and above 1 h,30 min of treatment with melatonin, with a peak at $10^{-14}$ M, the concentration at which a 60% increase was observed relative to the untreated control.

Stimulation of the expression of GSH-Px

Normal human keratinocytes were incubated for increasing periods (1 h,30 min, 3 h and 6 h) in the presence of melatonin at concentrations ranging from $10^{-6}$ to $10^{-17}$ M. The control corresponded to keratinocytes incubated in the absence of melatonin.

The level of expression of GSH-Px was measured after RT-PCR of the mRNA of GSH-Px. The level of expression of GSH-Px for each experimental condition was adjusted to that of actin, which represented the internal control.

An increase in the level of expression of GSH-Px was observed after incubation for 1 h,30 min with melatonin, with a peak at $10^{-15}$ M (60% increase). This increase was found after incubating for 3 h and 6 h, with a lower percentage at 6 h (40%).

These results demonstrate a stimulation of GSH-Px by melatonin at physiological concentrations (as low as $10^{-17}$ M) of hormonal type with an optimal dose at $10^{-14}$ and $10^{-15}$ M.

EXAMPLE 3

Study on normal human fibroblasts in culture

Fibroblasts were obtained by the technique of culturing explants. The cells were inoculated in 6-well culture plates. The fibroblast culture medium (FCM) comprised DMEM/M199 medium (3/1 v/v) supplemented with glutamine (2 mM), penicillin (50 IU/ml), streptomycin (50 μg/ml), sodium bicarbonate (0.2% w/v) and fetal calf serum (10% v/v).

The fibroblasts were incubated in the FCM medium at 37° C. under a humid atmosphere containing 5% $CO_2$, to the stage of confluence of the monolayers. They were incubated in the presence of iron-NTA in order to initiate production of the hydroperoxides which are responsible for a considerable level of radical attack.

The reference compounds were vitamin E acetate at 1 mg/ml (reference 1) and deferoxamine at 6.5 mg/ml (reference 2).

The melatonin and the reference compounds were dissolved directly in the buffer containing the fluorescent probe at 5 μM (CM-H2DCF-DA).

The fibroblasts were incubated with the melatonin or the reference compounds for one hour before the addition of iron-NTA, and then during the incubation in the presence of iron-NTA.

Control fibroblasts were cultured in the absence of melatonin or reference compounds, in the presence or absence or iron-NTA.

After incubation with the iron-NTA, the fibroblasts were washed by addition of medium and were then lysed by the action of ultrasound. The cell lysates were transferred into 96-well plates. In the presence of hydroperoxides, the probe CM-H2DCF-DA became fluorescent (A. S. Keston and R. Brandt, *Anal. Biochem.*, 11, 1–5 (1965)). The fluorescence of the probe was measured by fluorimetry using a plate analyzer (excitation: 355 nm, emission: 460 nm).

The results are reported in Table II below, compared to controls cultured in the absence of melatonin, with or without iron-NTA, and to two reference compounds.

TABLE II

| Melatonin Concentration (M) | Fluorescence units measured | % Protection |
|---|---|---|
| $10^{-7}$ M | 6539 ± 1413 | 86.9 |
| $10^{-8}$ M | 4940 ± 1045 | 100 |
| $10^{-9}$ M | 5655 ± 997 | 100 |
| $10^{-10}$ M | 5043 ± 705 | 100 |
| $10^{-11}$ M | 4817 ± 1141 | 100 |
| control without Fe-NTA | 5721 ± 607 | — |
| control with Fe-NTA | 11958 ± 1573 | — |
| reference 1 | 4197 ± 443 | 100 |
| reference 2 | 5688 ± 264 | 100 |

The above results confirm the antioxidant activity of melatonin at physiological concentrations, the percentages of protection obtained being equivalent to those observed for the two reference compounds employed at much higher concentrations (of about $10^{-2}$ M).

Composition examples

The following examples illustrate specific compositions according to the invention. In said compositions, the proportions indicated are percentages by weight.

EXAMPLE 4

| Facial care cream (oil-in-water emulsion): | |
|---|---|
| 6-Hydroxy-melatonin | $0.5 \times 10^{-6}$ |
| Glyceryl stearate | 2.00 |
| Polysorbate 60 (Tween 60 marketed by ICI) | 1.00 |
| Stearic acid | 1.40 |
| Triethanolamine | 0.70 |

-continued

| Facial care cream (oil-in-water emulsion): | |
|---|---|
| Carbomer | 0.40 |
| Liquid fraction of karite butter | 12.00 |
| Perhydrosqualene | 12.00 |
| Antioxidant | 0.05 |
| Fragrance | 0.5 |
| Preservative | 0.30 |
| Water | qs 100% |

EXAMPLE 5

| Care lotion: | |
|---|---|
| Melatonin | $1 \times 10^{-6}$ |
| Glycerol | 2 00 |
| Methylparaben | 0.15 |
| Fragrance | qs |
| Sterile demineralized water | qs 100% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable dermocosmetic composition for improving or maintaining the appearance of human skin or the scalp, comprising a minor antioxidant effective amount of melatonin or analog thereof, formulated into a topically applicable, cosmetically/dermatologically vehicle, diluent or carrier therefor, wherein said minor antioxidant effective amount is $10^{-15}\%$ to $10^{-7}\%$ by weight relative to the total weight of said composition.

2. The dermocosmetic composition as defined by claim 1, said minor antioxidant effective amount ranging from $10^{-12}\%$ to $10^{-15}\%$ by weight relative to the total weight thereof.

3. The dermocosmetic composition as defined by claim 1, comprising melatonin.

4. The dermocosmetic composition as defined by claim 1, comprising 5-methoxytryptamine, 5-methoxytryptophan, 5-methoxytryptophol, 5-methoxyindole-3-acetic acid or 6-hydroxymelatonin.

5. The dermocosmetic composition as defined by claim 1, comprising a melatoninergic agonist.

6. The dermocosmetic composition as defined by claim 1, comprising a solution, suspension, dispersion, lotion, serum, emulsion, milk, cream, gel, ointment, mousse, cleansing soap or bar, aerosol, microcapsules, microparticles, or vesicle dispersion.

7. The dermocosmetic composition as defined by claim 6, comprising an emulsion.

8. The dermocosmetic composition as defined by claim 1, comprising at least one conventional dermocosmetic additive or adjuvant.

9. A regimen for improving or maintaining the appearance of human skin or the scalp, comprising topically applying and delivering thereinto a minor antioxidant effective amount of melatonin or analog thereof, said minor antioxidant effective amount ranging from $10^{-15}$ to $10^{-7}$ M.

10. A regimen for improving or maintaining the appearance of human skin or the scalp, comprising topically applying and delivering thereinto an effective amount of the dermocosmetic composition as defined by claim 2.

11. A regimen for improving or maintaining the appearance of human skin or the scalp, comprising topically applying and delivering thereinto an effective amount of the dermocosmetic composition as defined by claim 3.

12. A regimen for improving or maintaining the appearance of human skin or the scalp, comprising topically applying and delivering thereinto an effective amount of the dermocosmetic composition as defined by claim 4.

13. A regimen for improving or maintaining the appearance of human skin or the scalp, comprising topically applying and delivering thereinto an effective amount of the dermocosmetic composition as defined by claim 5.

* * * * *